United States Patent
Ko et al.

(10) Patent No.: US 11,779,228 B2
(45) Date of Patent: Oct. 10, 2023

(54) BIO-SIGNAL MEASUREMENT APPARATUS AND BLOOD PRESSURE MEASUREMENT APPARATUS AND METHOD

(71) Applicant: SAMSUNG ELECTRONICS CO., LTD., Suwon-si (KR)

(72) Inventors: Byung Hoon Ko, Hwaseong-si (KR); Yong Joo Kwon, Yongin-si (KR); Young Soo Kim, Seoul (KR); Sang Yun Park, Hwaseong-si (KR); Jong Wook Lee, Suwon-si (KR); Chang Mok Choi, Suwon-si (KR); Jae Min Kang, Seoul (KR); Youn Ho Kim, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 591 days.

(21) Appl. No.: 16/422,220

(22) Filed: May 24, 2019

(65) Prior Publication Data
US 2019/0357780 A1    Nov. 28, 2019

(30) Foreign Application Priority Data
May 25, 2018    (KR) .................. 10-2018-0059802

(51) Int. Cl.
*A61B 5/021* (2006.01)
*A61B 5/00* (2006.01)

(52) U.S. Cl.
CPC ........ *A61B 5/02108* (2013.01); *A61B 5/6826* (2013.01); *A61B 5/6843* (2013.01); *A61B 2562/0247* (2013.01)

(58) Field of Classification Search
CPC . A61B 5/02108; A61B 5/6843; A61B 5/6826; A61B 2562/0247;
(Continued)

(56) References Cited

U.S. PATENT DOCUMENTS

| 10,398,324 | B2 | 9/2019 | Mukkamala et al. |
| 11,179,047 | B2 | 11/2021 | Mukkamala et al. |

(Continued)

FOREIGN PATENT DOCUMENTS

| JP | 2019170541 A | * 10/2019 | ........... A61B 5/0075 |
| KR | 10-2006-0081166 A | 7/2006 | |

(Continued)

OTHER PUBLICATIONS

Communication dated Nov. 14, 2022 issued by the Korean Intellectual Property Office in the Korean English Application No. 10-2018-0059802.

*Primary Examiner* — Gary Jackson
*Assistant Examiner* — Sebastian X Lukjan
(74) *Attorney, Agent, or Firm* — Sughrue Mion, PLLC

(57) ABSTRACT

A bio-signal measurement apparatus may include a first substrate and a second substrate, an optical sensor mounted in the first substrate, a force sensor disposed on or below the first substrate, and a separation structure interposed between the first substrate and the second substrate so as to prevent transmission of a force between the first substrate and the second substrate. An upper surface of the first substrate and an upper surface of the second substrate may be provided at the same level.

18 Claims, 11 Drawing Sheets

(58) Field of Classification Search
CPC ............ A61B 1562/043; A61B 5/6898; A61B 5/0077; A61B 5/681; A61B 5/6831; A61B 5/02433; A61B 5/0004
See application file for complete search history.

(56) References Cited

U.S. PATENT DOCUMENTS

| | | | |
|---|---|---|---|
| 2011/0166459 A1* | 7/2011 | Kopetsch | A61B 5/021 |
| | | | 600/485 |
| 2013/0296714 A1 | 11/2013 | Kassim et al. | |
| 2016/0058312 A1 | 3/2016 | Han et al. | |
| 2017/0020399 A1* | 1/2017 | Shemesh | A61B 5/0205 |
| 2017/0086688 A1* | 3/2017 | Masuda | A61B 5/02427 |
| 2017/0238819 A1* | 8/2017 | Waller | A61B 5/4875 |
| 2017/0251935 A1 | 9/2017 | Yuen | |
| 2017/0319146 A1 | 11/2017 | Park et al. | |
| 2018/0000413 A1* | 1/2018 | Masuda | A61B 5/02438 |
| 2018/0353075 A1* | 12/2018 | Duval | G01J 3/2803 |
| 2021/0298618 A1 | 9/2021 | Mukkamala et al. | |

FOREIGN PATENT DOCUMENTS

| | | |
|---|---|---|
| KR | 10-2006-0081178 A | 7/2006 |
| KR | 101000467 B1 | 12/2010 |
| KR | 10-1693469 B1 | 1/2017 |
| KR | 10-2017-0104419 A | 9/2017 |
| KR | 1020170124943 A | 11/2017 |
| WO | 2017152098 A1 | 9/2017 |
| WO | WO-2017152098 A1 * | 9/2017 ........... A61B 5/6898 |

* cited by examiner

BIO-SIGNAL MEASUREMENT APPARATUS AND BLOOD PRESSURE MEASUREMENT APPARATUS AND METHOD

CROSS-REFERENCE TO RELATED APPLICATION(S)

This application is based on and claims priority under 35 U.S.C. § 119(a) to Korean Patent Application No. 10-2018-0059802, filed on May 25, 2018, in the Korean Intellectual Property Office, the disclosure of which is incorporated herein by reference in its entirety.

BACKGROUND

1. Field

Example embodiments of the present disclosure relate to an apparatus for measuring a bio-signal.

2. Description of Related Art

Healthcare technology has attracted much attention due to the rapid entry into an aging society and relevant social problems such as increase in medical expenses. Accordingly, not only medical devices that can be utilized by hospitals and inspection agencies but also small-sized portable and/or wearable medical devices are being developed.

In addition, such a small-sized medical device is worn by a user in the form of a wearable device capable of directly measuring cardiovascular health status, such as blood pressure or the like, so that the user can directly measure and manage cardiovascular health status.

Therefore, research on miniaturization of a device for measuring cardiovascular health status, such as blood pressure or the like, have been actively conducted.

SUMMARY

Provided are a bio-signal measurement apparatus and a blood pressure measurement apparatus and method.

In accordance with an aspect of an example embodiment, there is provided a bio-signal measurement apparatus including: a first substrate and a second substrate, an upper surface of the first substrate and an upper surface of the second substrate being disposed at a same level; an optical sensor provided in the first substrate; a force sensor provided below the optical sensor; and a separation structure interposed between the first substrate and the second substrate and configured to prevent transmission of a force between the first substrate and the second substrate.

The second substrate may include two sub-substrates, and the first substrate is provided between the two sub-second substrates.

The second substrate may include three or more sub-substrates, and the three or more sub-substrates are disposed to surround the first substrate.

The second substrate may have a ring shape and surrounds the first substrate.

The separation structure may include a rail guide or an incompressible material.

The first substrate and the second substrate may be disposed to be simultaneously touchable by a single finger of a user.

The separation structure may be in contact with the first substrate and the second substrate.

The optical sensor may be configured to emit a light, and the first substrate, the second substrate, and the separation structure may be arranged in a direction perpendicular to a light emission direction in which the light is emitted from the optical sensor.

The separation structure may block the transmission of the force from the first substrate to the second substrate, in the direction perpendicular to the light emission direction.

In accordance with an aspect of an example embodiment, there is provided a bio-signal measurement apparatus including: a plurality of substrates provided at a same level; a plurality of substrates formed at the same height; a plurality of force sensors each of which is provided below each of the plurality of substrates; and a plurality of separation structures each of which is provided between the plurality of substrates and configured to prevent transmission of force between the substrates.

The plurality of substrates may be arranged in a straight line.

The plurality of substrates may be arranged in a lattice pattern.

Each of the separation structures is formed of a rail guide or an incompressible material.

In accordance with an aspect of an example embodiment, there is provided a blood pressure measurement apparatus including: a bio-signal measurer comprising a first substrate and a second substrate, an upper surface of the first substrate and an upper surface of the second substrate are disposed at a same level, an optical sensor provided in the first substrate, a force sensor provided below the optical sensor, and a separation structure interposed between the first substrate and the second substrate so as to prevent transmission of a force between the first substrate and the second substrate, and configured to measure a pulse wave signal of a user, by using the optical sensor when the user in contact with the first substrate and measure the force applied to the first substrate by the user using the force sensor; and a processor configured to estimate a blood pressure of the user based on the measured pulse wave signal and the measured force.

The processor may calculate a contact pressure between the user and the first substrate based on the measured force and an area of the upper surface of the first substrate and estimate the blood pressure based on the calculated contact pressure and the measured pulse wave signal.

Other features and aspects will be apparent from the following detailed description, the drawings, and the claims.

BRIEF DESCRIPTION OF THE DRAWINGS

The above and/or other aspects will be more apparent from the following description of example embodiments taken in conjunction with the accompanying drawings, in which.

Figure 1:
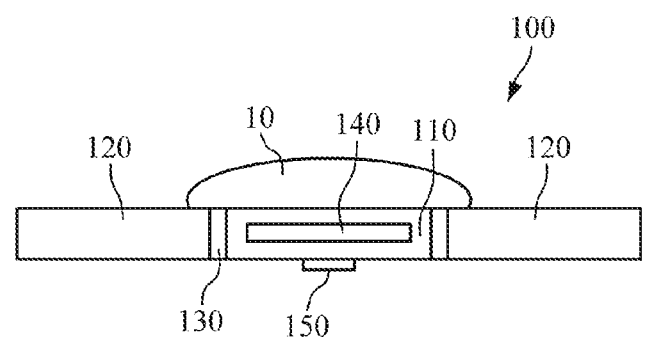
FIG. 1 is a diagram illustrating a bio-signal measurement apparatus according to an example embodiment.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

Example embodiments are described in greater detail below with reference to the accompanying drawings. In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

It should be noted that in some alternative implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved.

It will be understood that, although the terms first, second, etc. may be used herein to describe various elements, these elements should not be limited by these terms. These terms are only used to distinguish one element from another. Also, the singular forms are intended to include the plural forms as well, unless the context clearly indicates otherwise. In the specification, unless explicitly described to the contrary, the word "comprise" and variations such as "comprises" or "comprising," will be understood to imply the inclusion of stated elements but not the exclusion of any other elements. Terms such as " . . . unit" and "module" denote units that process at least one function or operation, and they may be implemented by using hardware, software, or a combination of hardware and software.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

It will also be understood that the elements or components in the following description are discriminated in accordance with their respective main functions. In other words, two or more elements may be made into one element or one element may be divided into two or more elements in accordance with a subdivided function. Additionally, each of the elements in the following description may perform a part or whole of the function of another element as well as its main function, and some of the main functions of each of the elements may be performed exclusively by other elements. Each element may be realized in the form of a hardware component, a software component, and/or a combination thereof.

FIG. 1 is a diagram illustrating a bio-signal measurement apparatus according to an example embodiment. The bio-signal measurement apparatus 100 of FIG. 1 may be mounted in an electronic device. In addition, the bio-signal measurement apparatus 100 may be formed as a separate device surrounded by a housing. In particular, examples of the electronic device may include a mobile phone, a smartphone, a tablet computer, notebook computer, a personal digital assistant (PDA), a portable multimedia player (PMP), a navigation system, an MP3 player, a digital camera, a wearable device, and the like, and the wearable device may include wearable devices of a wrist type, a wrist band type, a ring type, a belt type, a necklace type, an ankle band type, a thigh band type, a forearm band type, and the like. However, the electronic device is not limited to the above examples and the wearable device is not also limited to the above examples.

Referring to FIG. 1, the bio-signal measurement apparatus 100 may include a first substrate 110, a second substrate 120, a separation structure 130, an optical sensor 140, and a force sensor 150.

The first substrate 110 and the second substrate 120 may be formed such that upper surfaces thereof are at the same height. In addition, the first substrate 110 and the second substrate 120 may be disposed close to each other such that both the first and second substrates 110 and 120 can be brought in contact with one finger of a user.

The separation structure 130 may be interposed between the first substrate 110 and the second substrate 120. The separation structure 130 may block the transmission of force between the first substrate 110 and the second substrate 120 such that force exerted on the upper surface of the first substrate 110 is not transmitted to the second substrate 120 and force exerted on the upper surface of the second substrate 120 is not transmitted to the first substrate 110. According to an example embodiment, the separation structure 130 may be formed of a rail guide or an incompressible material (e.g., rubber, fluid, or the like).

The optical sensor 140 may be mounted in the first substrate 110 to emit light to the user's finger 10 in contact with the first substrate 110 and receive light returning from the finger 10.

A light emitter of the optical sensor 140 may emit light to the user's finger 10 in contact with the first substrate 110. The light emitter may include one or more light sources formed with a light emitting diode (LED), a laser diode, or a fluorescent body.

According to an example embodiment, the light source may emit visible light, near infrared ray (NIR) light, or mid infrared ray (MIR) light. However, a wavelength of light emitted from the light source may vary according to the purpose of measurement or a type of component of interest to be analyzed. In addition, the light source is not necessarily configured as a single light emitting body, and may be formed as an array of a plurality of light emitting bodies.

A light receiver of the optical sensor 140 may receive light reflected or scattered from the finger 10 of the user. The light receiver may include a photodetector formed with a photo diode, a photo transistor (PTr), a charge-coupled device (CCD), or the like. The photodetector is not necessarily configured as a single device, and may be configured as an array of a plurality of devices.

The number and arrangement of the light sources and the photodetectors may vary according to the application purpose of the optical sensor 140 and the size and shape of the electronic device in which the optical sensor 140 is mounted.

The force sensor 150 may be disposed below the first substrate 110 and measure a force exerted on the first substrate 110 by the user's finger 10. The first substrate 110 may include an upper surface and a lower surface opposing the upper surface. The upper surface may be provided as a contact surface that is touchable by the user. The force sensor 150 may be disposed on or below the lower surface of the first substrate 110, so as to oppose the front surface of the first substrate 110. In another embodiment, the force sensor 150 may be disposed in the first substrate, below the optical sensor 140.

As shown in FIG. 1, the first substrate 110, the second substrate 120, and the separation structure 130 may be arranged in a direction (e.g., a horizontal direction) perpendicular to a light emission direction (e.g., a vertical direction) in which the light is emitted from the optical sensor 140.

The separation structure 120 may prevent the force from being transmitted from the first substrate 110 to the second substrate 120, in the direction perpendicular to the light emission direction.

Figure 2:
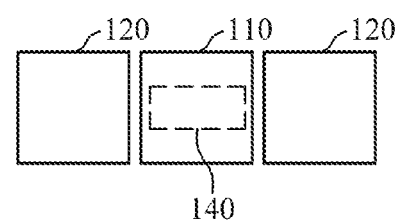
FIGS. 2 to 4 are diagrams illustrating examples of arrangement of a first substrate and a second substrate of the bio-signal measurement apparatus.
Figure 3:
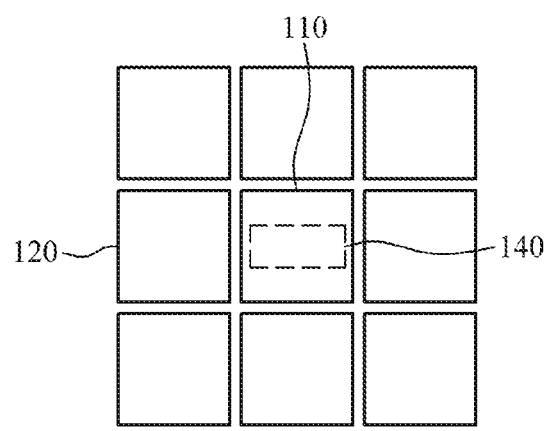
Figure 4:
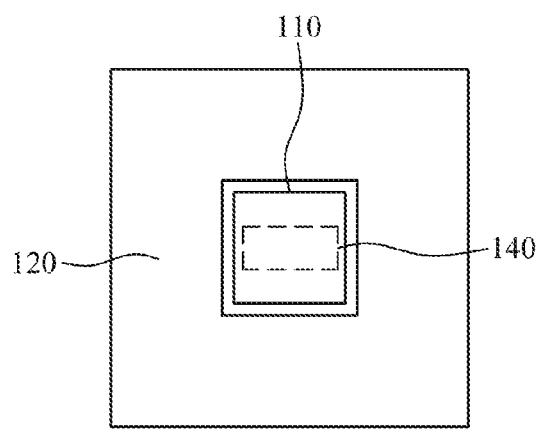

FIGS. 2 to 4 are diagrams illustrating examples of arrangement of the first substrate 110 and the second substrate 120 of the bio-signal measurement apparatus 100. In FIGS. 2 to 4, for convenience of description, it is illustrated that the separation structure 130 is omitted and the first substrate 110 and the second substrate 120 are physically spaced apart from each other.

Referring to FIG. 2, the bio-signal measurement apparatus 100 according to an example embodiment may include two second substrates 120 and a first substrate 110 in which the optical sensor 140 is mounted may be interposed between the two second substrate 120. The upper surfaces of the first substrate 110 and the two second substrates 120 may be disposed at the same level.

Referring to FIG. 3, the bio-signal measurement apparatus 100 may include eight second substrates 120, and the eight second substrates 120 may be disposed to surround a first substrate 110 in which the optical sensor 140 is mounted. The upper surfaces of the first substrate 110 and the eight second substrates 120 may be disposed at the same level.

Referring to FIG. 4, the bio-signal measurement apparatus 100 according to still another example embodiment may include a single second substrate 120, and the second substrate 120 may be formed in a ring shape to surround a first substrate 110.

In FIG. 4, the first substrate 110 has a square/rectangular shape and the second substrate 120 has a square/rectangular ring shape, but the shapes of the first substrate 110 and the second substrate 120 are not limited thereto. For example, the first substrate 110 may have a circle shape and the second substrate 120 may have a round ring shape.

FIGS. 2, 3, and 4 are merely examples of the arrangement of the first substrate 110 and the second substrate 120. That is, the number and arrangement of the first substrate 110 and the second substrate 120 may vary according to the application purpose of the bio-signal measurement apparatus 100 and the size and shape of the electronic device in which the bio-signal measurement apparatus 100 is mounted.

Figure 5:
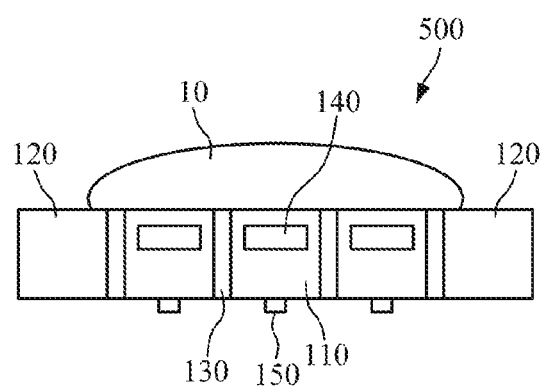
FIG. 5 is a diagram illustrating a bio-signal measurement apparatus according to another example embodiment.

FIG. 5 is a diagram illustrating a bio-signal measurement apparatus according to another example embodiment. The bio-signal measurement apparatus 500 of FIG. 5 may be mounted in an electronic device. In addition, the bio-signal measurement apparatus 500 may be formed as a separate device surrounded by a housing. In this case, examples of the electronic device may include a mobile phone, a smartphone, a tablet computer, notebook computer, a PDA, a PMP, a navigation system, an MP3 player, a digital camera, a wearable device, and the like, and the wearable device may include wearable devices of a wrist type, a wrist band type, a ring type, a belt type, a necklace type, an ankle band type, a thigh band type, a forearm band type, and the like. However, the electronic device is not limited to the above examples and the wearable device is not also limited to the above examples.

Referring to FIG. 5, the bio-signal measurement apparatus 500 may include a plurality of first substrates 110 and second substrates 120, separation structures 130, a plurality of optical sensors 140, and a plurality of force sensors 150.

The plurality of first substrates 110 and second substrates 120 may be formed such that upper surfaces thereof are at the same height. In addition, the plurality of first substrates 110 and second substrates 120 may be disposed close to each other such that both the first and second substrates 110 and 120 can be brought in contact with one finger of a user.

The separation structures 130 may be interposed between the first substrates 110 and between the first substrate 110 and the second substrate 120. The separation structures 130 may prevent transmission of force between the first substrates 110 and between the first substrate 110 and the second substrate 120 such that a force exerted on the top of the first substrate 110 is not transmitted to other first substrates 110 and the second substrates 120 and a force exerted on the top of the second substrate 120 is not transmitted to the first substrate 110. According to an example embodiment, the separation structures 130 may each be formed of a rail guide or an incompressible material (e.g., rubber, fluid, or the like).

The optical sensors 140 may be mounted in each of the first substrates 110 and may emit light to the user's finger 10 in contact with the first substrate 110 and receive light returning from the finger 10.

The force sensors 150 may be disposed below each of the first substrates 110 and may measure a force applied to the first substrate 110 by the user's finger 10.

Figure 6:
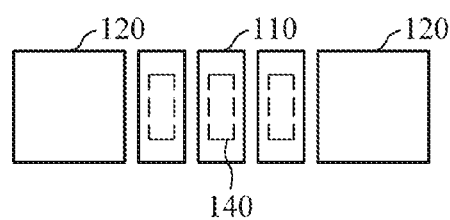
FIGS. 6 to 8 are diagrams illustrating examples of arrangement of first substrates and second substrates of the bio-signal measurement apparatus.
Figure 7:
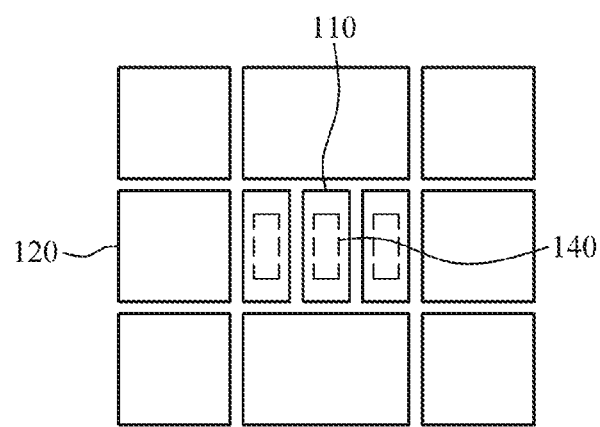
Figure 8:
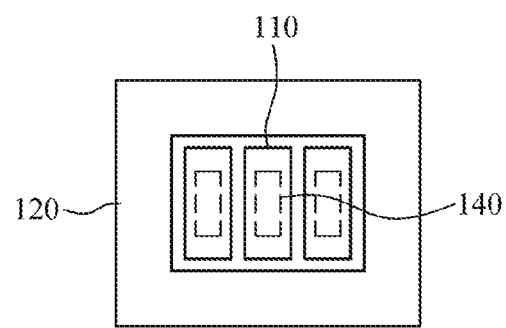

FIGS. 6 to 8 are diagrams illustrating examples of arrangement of the first substrates 110 and the second substrates 120 of the bio-signal measurement apparatus 500. In FIGS. 6 to 8, for convenience of explanation, the separation structures 130 are omitted and the first substrates 110 and the second substrates 120 are illustrated as being physically spaced apart from each other.

Referring to FIG. 6, the bio-signal measurement apparatus 500 according to an example embodiment may include two second substrates 120 and a plurality of first substrates 110 interposed between the two second substrates 120, wherein the plurality of first substrates 110 in each of which the optical sensor 140 is mounted are arranged in a straight line.

Referring to FIG. 7, the bio-signal measurement apparatus 500 according to another example embodiment may include eight second substrates 120 and a plurality of first substrates 110 in each of which an optical sensor 140 is mounted may be arranged in a lattice pattern. In this case, the eight second substrates 120 may be disposed to surround the plurality of first substrates 110 arranged in a lattice pattern.

Referring to FIG. 8, the bio-signal measurement apparatus 500 according to still another example embodiment may include one second substrate 120 which is formed in a ring shape and surrounds a plurality of first substrates 110 in each of which an optical sensor 140 is mounted.

FIGS. 6, 7, and 8 are merely examples of the arrangement of the first substrates 110 and the second substrates 120 and the number of second substrates 120. That is, the number and arrangement of the first substrates 110 and the second substrates 120 may vary according to the application purpose of the bio-signal measurement apparatus 500 and the size and shape of the electronic device in which the bio-signal measurement apparatus 500 is mounted.

Figure 9:
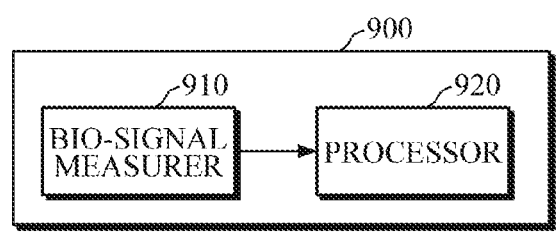
FIG. 9 is a block diagram illustrating a blood pressure measurement apparatus according to an example embodiment.

FIG. 9 is a block diagram illustrating a blood pressure measurement apparatus according to an example embodiment. FIG. 9 illustrates an example embodiment of an apparatus for measuring a blood pressure using the bio-signal measurement apparatus 100 or 500 described above with reference to FIGS. 1 to 8.

Referring to FIG. 9, the blood pressure measurement apparatus 900 may include a bio-signal measurer 910 and a processor 920. Here, the bio-signal measurer 910 may be an example embodiment of the bio-signal measurement apparatus 100 or 500 described above with reference to FIGS. 1 to 8.

The bio-signal measurer 910 may include an optical sensor 140 and a force sensor 150. The optical sensor 140 may emit light to a user's finger in contact with the first substrate 110 and receive light returning from the user's finger to measure a pulse wave signal of the user. In this case, the pulse wave signal may be a photoplethysmography (PPG) signal, and the optical sensor 140 may be a PPG sensor.

The force sensor 150 may be disposed below the first substrate 110, and may measure a force applied to the first substrate 110 by the user's finger.

The processor 920 may control an overall operation of the blood pressure measurement apparatus 900.

The processor 920 may activate the optical sensor 140 to emit a light to the user and detect the light reflected or scattered from the user, in response to determining that the first substrate 110 is in contact with the user.

The processor 920 may generate guide information for inducing the increase or decrease of a contact pressure between the user's finger and the first substrate 110 in response to a user's instruction and provide the guide information to the user. The processor may provide the guide information through an output interface, such as a display, a speaker, a tactile motor, and the like.

The processor 920 may estimate a user's blood pressure based on the measured pulse wave signal and the measured force. For example, the processor 920 may calculate a contact pressure between the user's finger and the first substrate 110 based on the force measured using the force sensor disposed below the first substrate 110 and the area of the upper surface of the first substrate 110. In addition, the processor 920 may estimate the user's blood pressure by analyzing the changes in pulse wave according to the change in contact pressure.

The blood pressure may include a diastolic blood pressure (DBP), a systolic blood pressure (SBP), and a mean arterial pressure (MAP) and the contact pressure applied on the user's finger may act as an external pressure on a blood vessel. When the contact pressure becomes smaller than the MAP, the elastic resilience of tissue acts in a direction of compressing the blood vessel and hence the amplitude of the pulse wave becomes small. When the contact pressure is equal to the MAP, the elastic resilience of tissue becomes zero and hence does not affect the blood vessel so that the amplitude of the pulse wave is maximized. In addition, when the contact pressure becomes greater than the MAP, the elastic resilience of tissue acts in a direction of expanding the blood vessel and hence the amplitude of the pulse wave becomes smaller. Therefore, the processor 920 may analyze changes in pulse wave in accordance with changes in contact pressure and estimate the MAP using the contact pressure at a point where the amplitude of the pulse wave is maximized.

In addition, the processor 920 may estimate the SBP using a contact pressure at a point where a ratio of an amplitude of the measured pulse wave to a predetermined maximum amplitude is a first ratio (e.g., 0.6) as an SBP, and estimate the DBP using a contact pressure at a point where a ratio of the amplitude of the measured pulse wave to the predetermined maximum amplitude is a second ratio (e.g. 0.7).

According to the example embodiment, a force applied as an input by the user's finger is transmitted to the first substrate 110 and the second substrate 120 in a distributed manner and the contact pressure is calculated using the force transmitted to the first substrate 110 and the area (fixed value) of the upper surface of the first substrate 110, so that it is possible to measure the contact pressure very similar to a pressure applied as an input and thereby improve the accuracy of blood pressure measurement.

Figure 10:
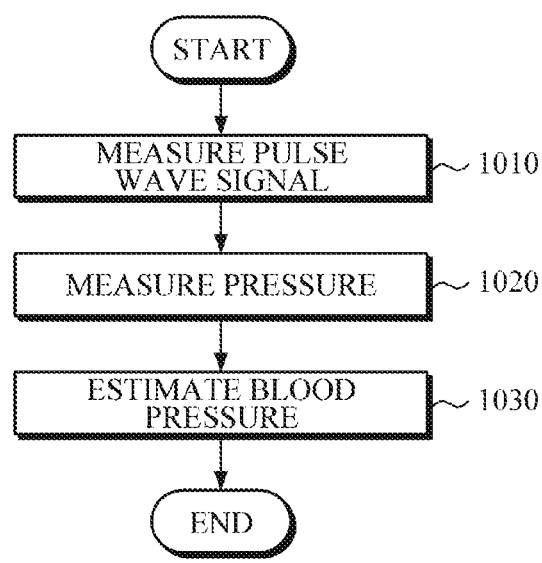
FIG. 10 is a flowchart illustrating a method of measuring blood pressure according to an example embodiment.

FIG. 10 is a flowchart illustrating a method of measuring blood pressure according to an example embodiment. The blood pressure measurement method illustrated in FIG. 10 may be performed by the blood pressure measurement apparatus 900 of FIG. 9.

Referring to FIGS. 9 and 10, in operation 1010, the blood pressure measurement apparatus 900 may emit light to a user's finger in contact with the first substrate 110 using the optical sensor mounted in the first substrate 110, receive light returning from the user's finger, and measure a pulse wave signal of the user. In this case, the pulse wave signal may be a PPG signal.

In operation 1020, the blood pressure measurement apparatus 900 may measure a force applied to the first substrate 110 by the user's finger using the force sensor disposed below the first substrate 110.

In operation 1030, the blood pressure measurement apparatus 900 may estimate a user's blood pressure based on the measured pulse wave signal and the measured force. For example, the blood pressure measurement apparatus 900 may calculate a contact pressure between the user's finger and the first substrate 110 based on the force measured using the force sensor disposed below the first substrate 110 and the area of an upper surface of the first substrate 110. In addition, the blood pressure measurement apparatus 900 may estimate the user's blood pressure by analyzing changes in pulse wave in accordance with changes in the contact pressure.

Figure 11:
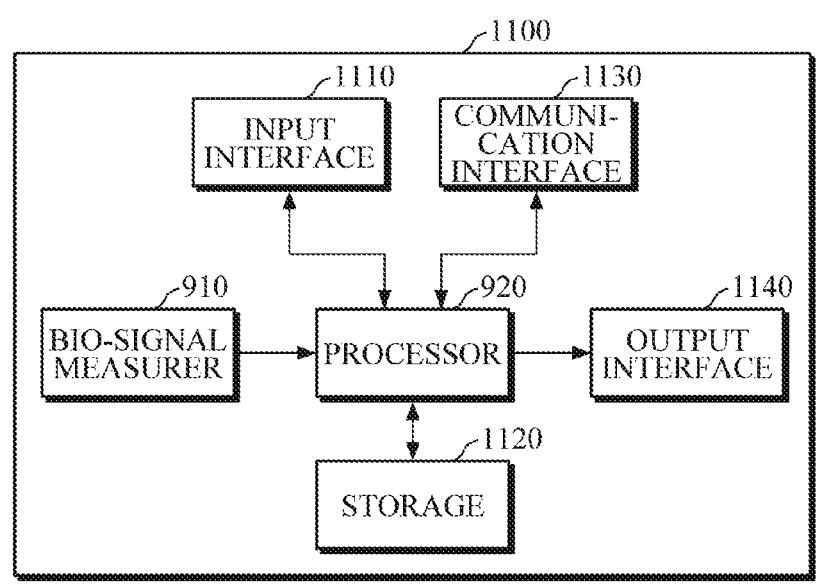
FIG. 11 is a block diagram illustrating a blood pressure measurement apparatus according to another example embodiment.

FIG. 11 is a block diagram illustrating a blood pressure measurement apparatus according to another example embodiment.

Referring to FIG. 11, the blood pressure measurement apparatus 1100 may include a bio-signal measurer 910, a processor 920, an input interface 1110, a storage 1120, a communication interface 1130, and an output interface 1140. In this case, the bio-signal measurer 910 and the processor 920 are the same as those described above with reference to FIG. 9 and thus detailed descriptions thereof will not be reiterated.

The input interface 1110 may receive various operation signals from a user. According to an example embodiment, the input interface 1110 may include a key pad, a dome switch, a resistive or capacitive touch pad, a jog wheel, a jog switch, a hardware (H/W) button, and the like. In particular, when a touch pad has a layered structure with a display, this structure may be referred to as a touch screen.

The input interface 1110 may receive user related information. Here, the user related information may include height, weight, age, etc. In this case, the processor 920 may correct the blood pressure according to the input user related information. A user-specific blood pressure estimation correlation model may be stored in the storage 1120 and the processor 920 may select a blood pressure estimation correlation model suitable for the corresponding user and correct the blood pressure using the selected blood pressure estimation correlation model.

Programs or instructions for operations of the blood pressure measurement apparatus 1100 may be stored in the storage 1120 and data input to and output from the blood pressure measurement apparatus 1100 may also be stored in the storage 1120. In addition, the storage 1120 may store data input by the user, data acquired or processed by the blood pressure measurement apparatus 1100, and information required for data processing of the blood pressure measurement apparatus 100.

The storage 1120 may include at least one type of storage media, such as a flash memory, a hard disk type memory, a multimedia card micro type memory, a card-type memory (e.g., SD or XD memory), random access memory (RAM), static random access memory (SRAM), read only memory (ROM), electrically erasable programmable read only memory (EEPROM), programmable read only memory (PROM), magnetic memory, and optical disk. In addition, the blood pressure measurement apparatus 1100 may operate an external storage medium, such as web storage providing a storage function of the storage 1120.

The communication interface 1130 may communicate with an external device. For example, the communication interface 1130 may transmit data input by the user, the data acquired or processed by the blood pressure measurement apparatus 1100, and the information required for data processing of the blood pressure measurement apparatus 1100 to the external device or may receive a variety of data useful to estimate the blood pressure from the external device.

Here, the external device may be medical equipment which uses the data input by the user, the data acquired or processed by the blood pressure measurement apparatus 1100, and the information required for data processing of the blood pressure measurement apparatus 1100, or may be a printer or display device to output a result. In addition, the external device may include, but not limited to, a digital TV, a desktop computer, a mobile phone, a smartphone, a tablet computer, a notebook computer, a PDA, a PMP, a navigation terminal, an MP3 player, a digital camera, a wearable device, and the like.

The communication interface 1130 may communicate with the external device using various communication technologies, such as Bluetooth, Bluetooth low energy (BLE), near field communication (NFC), wireless local area network (WLAN) communication, ZigBee communication, infrared data association (IrDA) communication, Wi-Fi direct (WFD) communication, ultra-wideband (UWB) communication, Ant+ communication, Wi-Fi communication, RFID communication, 3G communication, 4G communication, 5G communication, and the like. However, these are merely examples, and embodiments are not limited thereto.

The output interface 1140 may output the data input by the user, the data acquired or processed by the blood pressure measurement apparatus 1100, the information required for data processing of the blood pressure measurement apparatus 1100, and the like. According to an example embodiment, the output interface 1140 may output the data input by the user, the data acquired or processed by the blood pressure measurement apparatus 1100, and the information required for data processing of the blood pressure measurement apparatus 1100 in at least one of visual, audible, and tactile manners. To this end, the output interface 1140 may include a display, a speaker, a vibrator, and the like.

While not restricted thereto, embodiments can be implemented as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an example embodiment may be written as a computer program transmitted over a computer-readable transmission medium, such as a carrier wave, and received and implemented in general-use or special-purpose digital computers that execute the programs. Moreover, it is understood that in example embodiments, one or more units of the above-described apparatuses and devices can include circuitry, a processor, a microprocessor, etc., and may execute a computer program stored in a computer-readable medium.

The foregoing embodiments are merely examples and are not to be construed as limiting. The present teaching can be readily applied to other types of apparatuses. Also, the description of the example embodiments is intended to be illustrative, and not to limit the scope of the claims, and many alternatives, modifications, and variations will be apparent to those skilled in the art.

What is claimed is:

1. A bio-signal measurement apparatus comprising:
a first substrate;
a second substrate, an upper surface of the first substrate and an upper surface of the second substrate being disposed at a same level;
an optical sensor provided in the first substrate;
a force sensor provided below the optical sensor; and
a separation structure interposed between the first substrate and the second substrate at the same level as the first substrate and the second substrate, and configured to prevent a downward force exerted on a top surface of the first substrate from being horizontally transmitted from the first substrate to the second substrate.

2. The bio-signal measurement apparatus of claim 1, wherein the second substrate comprises two sub-substrates, and the first substrate is provided between the two sub-substrates, and
wherein the optical sensor is provided inside the first substrate, and the force sensor is disposed on a lower surface of the first substrate.

3. The bio-signal measurement apparatus of claim 1, wherein the second substrate comprises a first part and a second part that are separated from each other by the first substrate provided between the first part and the second part in a horizontal direction, and
the separation structure comprises:
a first separation structure interposed between the first substrate and the first part of the second substrate in the horizontal direction; and
a second separation structure interposed between the first substrate and the second part of the second substrate in the horizontal direction, wherein the first separation structure and the second separation structure.

4. The bio-signal measurement apparatus of claim 1, wherein the second substrate has a ring shape and surrounds an entire side surface of the first substrate.

5. The bio-signal measurement apparatus of claim 1, wherein the separation structure corresponds to a rail guide.

6. The bio-signal measurement apparatus of claim 1, wherein the first substrate and the second substrate are disposed to be simultaneously touchable by a single finger of a user.

7. The bio-signal measurement apparatus of claim 1, wherein the optical sensor and the force sensor are arranged in a vertical direction, and the first substrate, the second substrate, and the separation structure are arranged in a horizontal direction, and
wherein side surfaces of the separation structure are in contact with a side surface of the first substrate and a side surface of the second substrate, in the horizontal direction.

8. The bio-signal measurement apparatus of claim 1, wherein the optical sensor is configured to emit a light, and
wherein the first substrate, the second substrate, and the separation structure are arranged in a direction perpendicular to a light emission direction in which the light is emitted from the optical sensor.

9. The bio-signal measurement apparatus of claim 8, wherein the separation structure blocks transmission of the downward force from the first substrate to the second substrate, in the direction perpendicular to the light emission direction.

10. A bio-signal measurement apparatus comprising:
a plurality of substrates provided at a same level; a plurality of force sensors provided below each of the plurality of substrates; and
a plurality of separation structures provided between the plurality of substrates at the same level as the plurality of substrates, and configured to prevent a downward force exerted on a top surface of the plurality of substrates from being horizontally transmitted between the plurality of substrates,
wherein each of the plurality of separation structures corresponds to a rail guide.

11. The bio-signal measurement apparatus of claim 10, wherein the plurality of substrates is arranged in a straight line.

12. The bio-signal measurement apparatus of claim 10, wherein
the plurality of substrates is arranged in a lattice pattern.

13. A blood pressure measurement apparatus comprising:
a bio-signal measurer comprising:
a first substrate;
a second substrate, an upper surface of the first substrate and an upper surface of the second substrate are disposed at a same level;
an optical sensor provided in the first substrate;
a force sensor provided below the optical sensor; and
a separation structure provided between the first substrate and the second substrate at the same level as the first substrate and the second substrate, and configured to prevent a downward force exerted on a top surface of the first substrate from being horizontally transmitted from the first substrate to the second substrate, the bio-signal measurer being configured to measure a pulse wave signal of a user by using the optical sensor when the user is in contact with the first substrate, and measure the downward force applied to the first substrate by the user using the force sensor; and
a processor configured to estimate a blood pressure of the user based on the pulse wave signal and the downward force.

14. The blood pressure measurement apparatus of claim 13, wherein the processor is further configured to obtain a contact pressure between the user and the first substrate based on the downward force and an area of the upper surface of the first substrate, and estimate the blood pressure based on the contact pressure and the pulse wave signal.

15. The blood pressure measurement apparatus of claim 13, wherein the second substrate comprises two sub-substrates, and the first substrate is provided between the two sub-substrates.

16. The blood pressure measurement apparatus of claim 13, wherein the second substrate comprises a plurality of sub-substrates, and the plurality of sub-substrates surround the first substrate.

17. The blood pressure measurement apparatus of claim 13, wherein the second substrate has a ring shape and surrounds an entire side surface of the first substrate.

18. The blood pressure measurement apparatus of claim 13, wherein the separation structure corresponds to a rail guide.

* * * * *